(12) United States Patent
Sasady

(10) Patent No.: US 6,443,902 B1
(45) Date of Patent: Sep. 3, 2002

(54) ULTRASOUND PROBE WITH A DETACHABLE NEEDLE GUIDE, FOR COLLECTING TISSUE SAMPLES

(75) Inventor: Niels-Chr. Sasady, Nærum (DK)

(73) Assignee: B-K Medical A/S, Gentofte (DK)

( * ) Notice: Subject to any disclaimer, the term of this patent is extended or adjusted under 35 U.S.C. 154(b) by 0 days.

(21) Appl. No.: 09/582,663
(22) PCT Filed: Jan. 5, 1999
(86) PCT No.: PCT/DK99/00001
§ 371 (c)(1), (2), (4) Date: Jun. 29, 2000
(87) PCT Pub. No.: WO99/34735
PCT Pub. Date: Jul. 15, 1999

(30) Foreign Application Priority Data

Jan. 7, 1998 (DE) .......................................... 1998 0012

(51) Int. Cl.[7] ................................................. A61B 8/00
(52) U.S. Cl. ....................................................... 600/461
(58) Field of Search ................................. 600/437, 459, 600/471

(56) References Cited

U.S. PATENT DOCUMENTS

| | | | | |
|---|---|---|---|---|
| 4,469,106 A | * | 9/1984 | Harui .......................... | 600/461 |
| 4,742,829 A | * | 5/1988 | Law et al. ................... | 600/461 |
| 4,817,616 A | * | 4/1989 | Goldstein .................... | 600/463 |
| 4,838,506 A | * | 6/1989 | Cooper ........................ | 248/200 |
| 4,877,033 A | * | 10/1989 | Seitz, Jr. ..................... | 604/171 |
| 4,883,059 A | * | 11/1989 | Stedman et al. ............. | 600/437 |
| 4,911,173 A | * | 3/1990 | Terwilliger .................. | 600/463 |
| 5,090,414 A | | 2/1992 | Takano | |
| 5,235,987 A | | 8/1993 | Wolfe | |
| 5,494,039 A | * | 2/1996 | Onik et al. .................. | 600/461 |
| 6,095,981 A | * | 8/2000 | McGahan ..................... | 600/461 |
| 6,102,867 A | * | 8/2000 | Dietz et al. .................. | 600/461 |
| 6,261,234 B1 | * | 7/2001 | Lin .............................. | 600/461 |

* cited by examiner

Primary Examiner—Francis J. Jaworski
(74) Attorney, Agent, or Firm—Abelman, Frayne Schwab

(57) ABSTRACT

An apparatus for insertion into the human body and which comprises one or more optionally scanning transducers 17,18 and a needle guide 12, which can be operated from the outside. The needle guide 12 is used for collecting tissue samples from the human body. According to the invention the needle guide 12 is separate from the other part of the apparatus which for hygienic reasons is covered by a sterile sheath 14. The needle guide 12 is thus attached to the other part of the catheter via the sheath. In other words the needle guide 12 is arranged outside the sheath 14 in such a manner that the needle need not penetrate the sterile sheath 14, which otherwise would entail that the apparatus should be disinfected after use.

5 Claims, 3 Drawing Sheets

ULTRASOUND PROBE WITH A DETACHABLE NEEDLE GUIDE, FOR COLLECTING TISSUE SAMPLES

This application is the national phase of international application PCT/DK99/00001 filed Jan. 5.1999, which designated the U.S.

TECHNICAL FIELD

The invention relates to an apparatus for insertion into the human body and which comprises at least two scanning transducers of which at last one preferably scans in the longitudinal direction, and a needle guide, which can be operated from the outside and used for collecting tissue samples from the human body the needle guide being separate from the other part of the apparatus which for hygiene reasons is covered by a sterile sheath.

BACKGROUND ART

When inserted into a patient's anus, such an apparatus is able to locate the internal organs, such as the prostate. If a sample is to be obtained from the area adjacent the neck of the bladder, it is possible to collect the sample by inserting a needle from the outside, the needle holder being attached to the apparatus as shown in FIG. 1. However this requires that a local anaesthetic is applied to the insertion point of the needle, as the area close to the surface of the skin contains many sensory nerves. It is however desirable to avoid such a local anaesthetic. Accordingly it has been desired to insert the needle through the intestinal wall at the anus, confer FIG. 2, whereby a local anaesthetic is not required, as the internal organs are not that sensitive. At the same time it is desirable that the apparatus is covered by a sterile sheath in use such that subsequent disinfection thereof is avoided, naturally the sterile sheath must not be damaged by the needle guide.

U.S. Pat. No. 4,742,829 describes an ultrasound probe including an array of transducer elements for localizing a biopsy needle to be pushed forward in the longitudinal direction of the probe The applicability of such a probe is very limited if the inner organs of of interest are not positioned in the longitudinal direction of the probe.

BRIEF DESCRIPTION OF THE INVENTION

The object of the invention is thus to provide an apparatus with a needle guide which cannot damage a sterile sheath and which is more applicable. At the same time the needle is to be in a plane substantially in the longitudinal direction.

An apparatus of the above type is according to tie invention characterised in that the needle guide is retained by being pressed into an inclined recess in the other part of the apparatus after the sterile sheath has been arranged on die apparatus and is retained by means of a needle guide holder. The needle guide is thus attached to the part of the apparatus on the outer side of the sterile sheath such that the needle need not penetrate the sheath, which otherwise would entail that the apparatus should be disinfected after use. Due to the inclined fastening of the needle guide the apparatus is able to collect tissue samples in nearly all directions different from the longitudinal direction and due to the at least two scanning transducers not scanning in the same direction it is possible to locate the needle very precisely in space.

U.S. Pat. No. 5,235,987 illustrates a needle guide holder to be mounted on an ultrasonic scanning bead covered with a disposable sheath. The needle is placed in front of the scanning head and such in apparatus is therefore not suitable for insertion into the human body.

Optionally according to the invention the needle guide may be retained by means of a needle guide holder which is clipped firmly onto the other part of the apparatus after the sterile sheath has been arranged on the apparatus.

BRIEF DESCRIPTION OF THE DRAWINGS

The invention is explained in grater detail below with reference to the accompanying drawings, in which.

BEST MODE FOR CARRYING OUT THE INVENTION

Transrectal ultrasound scanning of the prostate is a valuable method for detection and monitoring of diseases in the prostate.

Figure 1:
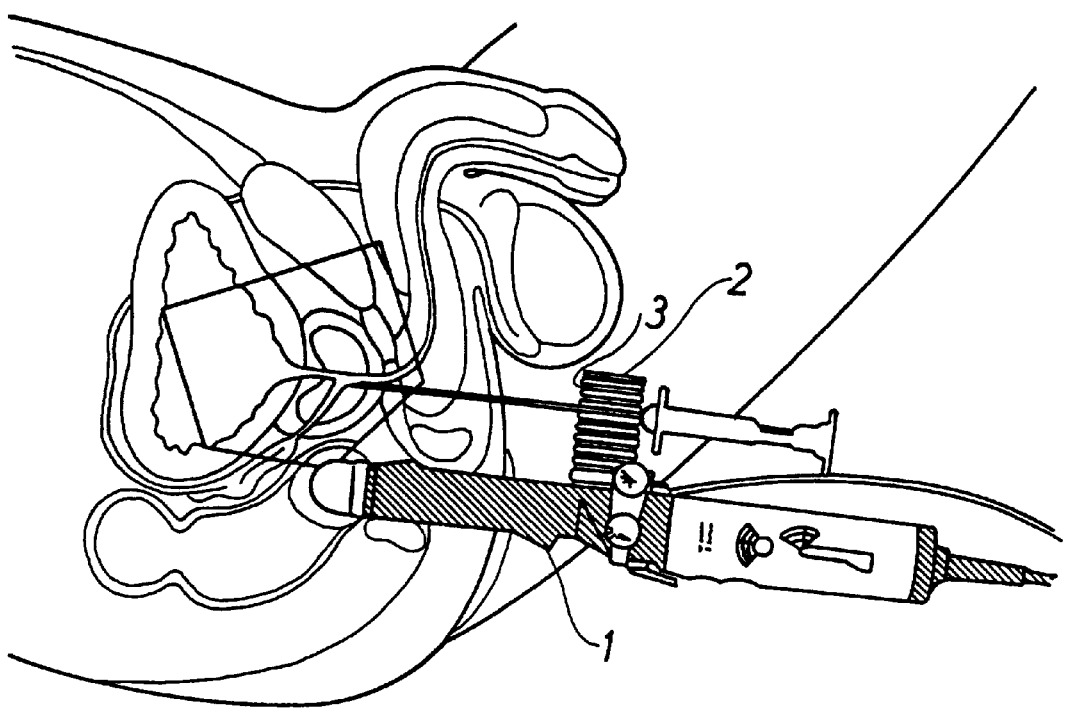
FIG. 1 shows a known apparatus for insertion into the human body.

FIG. 1 shows a known apparatus 1 for insertion into a patient's anus. By means of the apparatus an ultrasound scanning of for instance the prostate can be performed. Based on the ultrasound image of the prostate, a biopsy stylet is then inserted, a special holding member 2 for the stylet being attached to the apparatus. The holding member 2 ensures that the stylet is inserted substantially parallel to the apparatus 1. The holding member 2 is provided with a plurality of holes such that the suitable distance to the apparatus can be selected. During insertion, the stylet is visible on the ultrasound image. However it may be necessary to apply a local anaesthetic before inserting the stylet.

Figure 2:
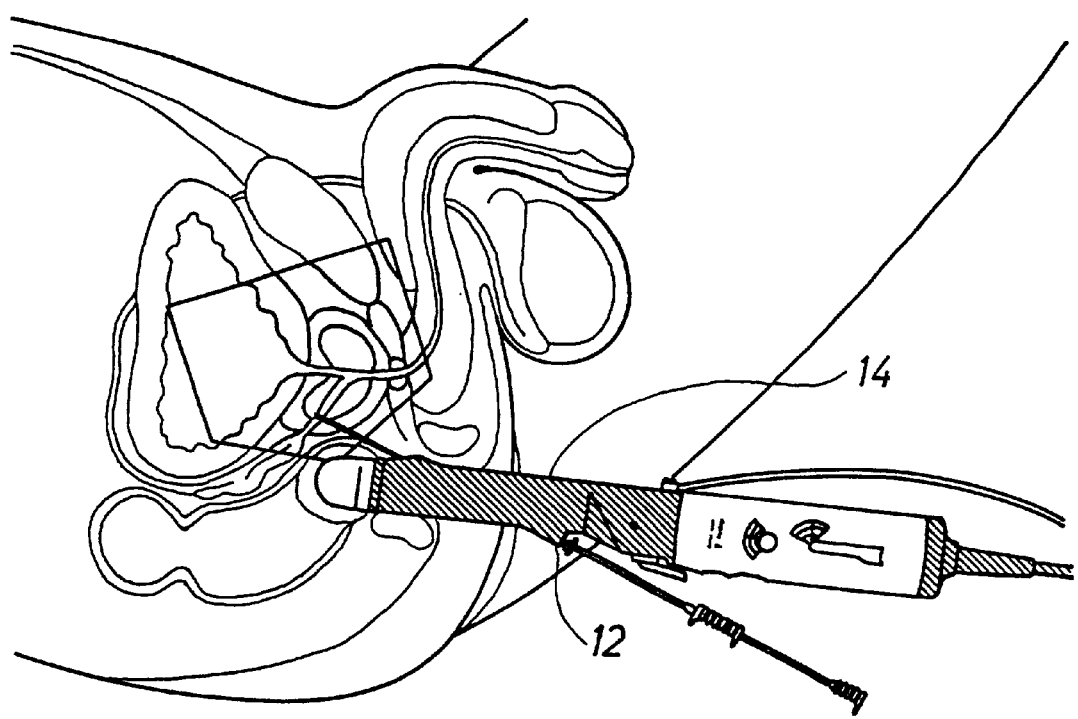
FIG. 2 shows an apparatus according to the invention for insertion into the human body.

FIG. 2 shows an apparatus according to the invention for insertion into the human body through the intestinal wall near the anus. At the end of the apparatus two ultrasonic transducers 17, 18 are provided; one ultrasonic transducer 17, which is able to scan in the longitudinal direction of the apparatus, and one ultrasonic transducer 18 which is able to scan across the longitudinal direction. As a result a fine image of the positioning of the patient's internal organs is obtained. It may be of interest to have a screen display of the precise position of the prostate.

The apparatus with the ultrasonic transducers 17, 18 is covered by a sterile sheath 14 such that the apparatus never comes into direct contact with the patient, whereby disinfection of the apparatus after use is not needed, as the apparatus is ready for reuse after a minor cleaning thereof when the sheath 14 has been removed. An inclining groove or recess is, however, provided on one side of the apparatus to receive a needle guide 12, after the sterile sheath 14 has been placed on the apparatus. Consequently, the needle guide 12 does not come into direct contact with the apparatus. The needle guide 12 is, however, retained in relation to the apparatus inter alia due to the additional friction caused by the sheath 14, said friction possibly being provided by means of indentations or grooves. Arranging the needle guide 12 in this manner is particularly advantageous in that the needle thus never penetrates the sheath 14. As a result the apparatus is not unnecessarily contaminated and thus need not be disinfected after each use.

After the apparatus with the needle guide 12 has been inserted into the anus and the internal organs in question have been located on the screen by means of the ultrasonic transducers 17, 18, a biopsy needle is inserted through the needle guide 12 and the penetration of the needle, until the needle tip reaches the organ, from which the sample is to be collected, is monitored on the screen[00ab] The biopsy needle is inserted through the needle guide 12 by hand.

When the desired number of samples has been collected, the needle and the entire apparatus are removed, whereafter it is sufficient to remove the needle guide 12 and the sheath 14 and clean the apparatus, which then is ready to be reused.

The ultrasonic transducers 17, 18 and the pertaining displays and electronic circuits are conventional types and are thus not described in detail.

Figure 3:
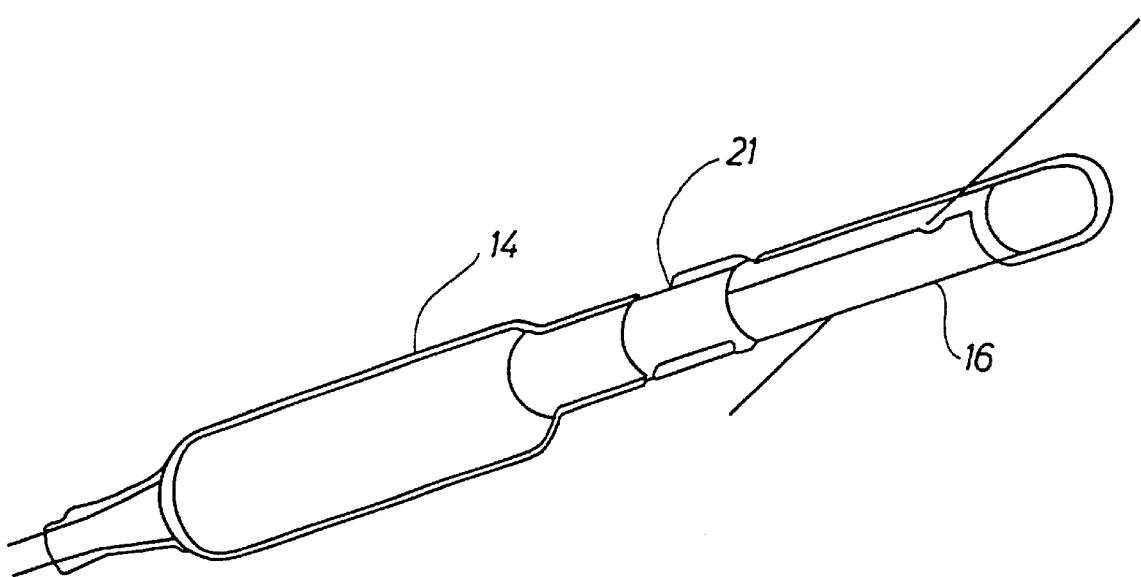
FIGS. 3 and 4 show an optional embodiment of the apparatus according to the invention in assembled and separated state.
Figure 4:
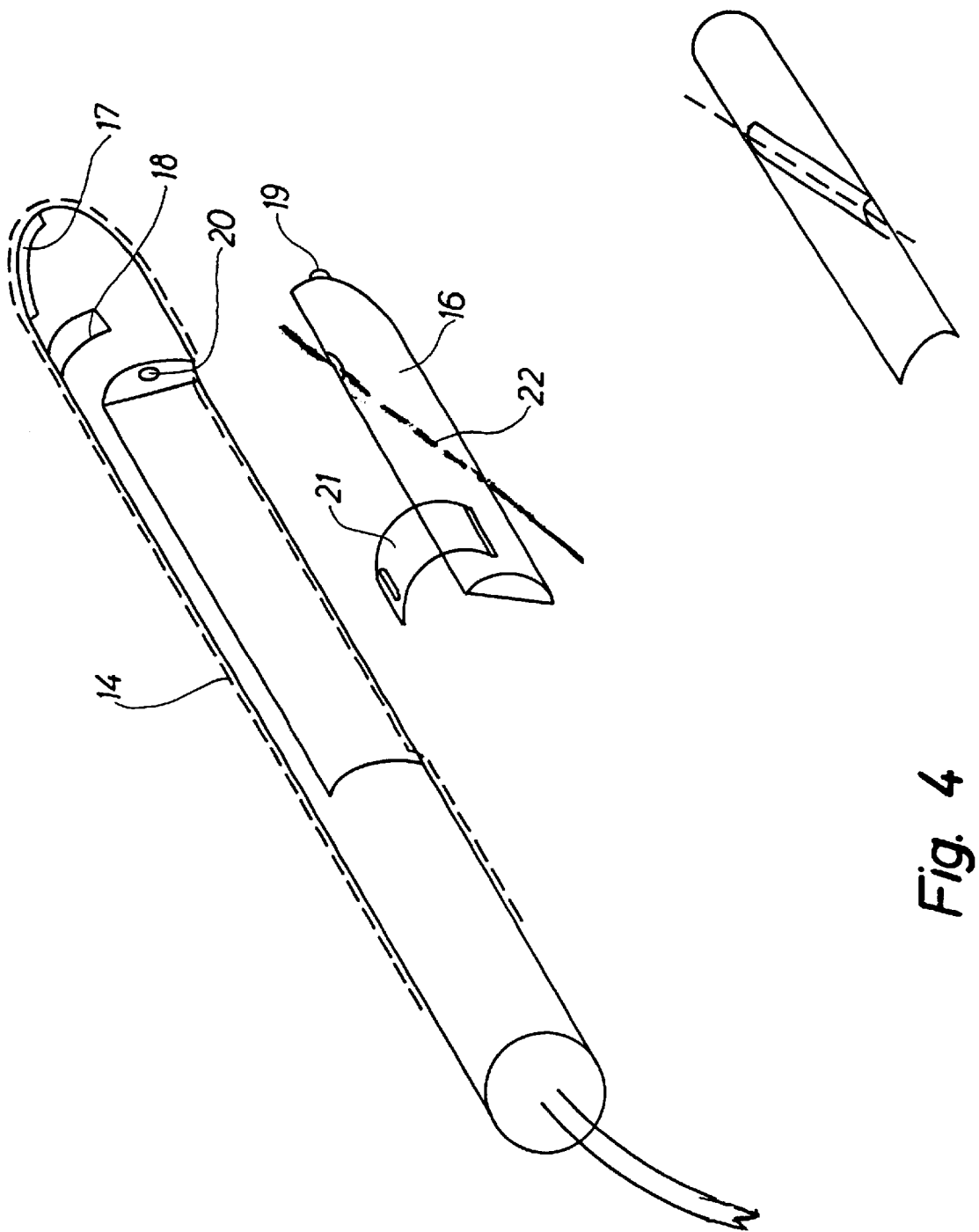

FIGS. 3 and 4 shows an optional embodiment of the apparatus, in which the needle guide 12 is retained by means of a separate needle guide holder 16. The needle guide holder is clipped firmly onto the other part of the catheter after the sterile sheath 14 has been arranged thereon and is formed of an oblong body of a material, which can be sterilised, such as stainless steel. The oblong body is formed as a sector of a circle in cross-section and substantially fits into a corresponding tap in the other part of the apparatus. The oblong body is provided with a projecting knot 19 mating with a corresponding opening 20 in the tap. When inserted into the opening 20, the needle guide holder is retained by being clipped thereon by means of special clipping member led partly around the apparatus. A groove 22, in which the needle guide 12 can be placed, is provided on the plane inner surface of the needle guide holder 16. The needle guide 12 is discarded after use, while the needle guide holder 16 may be disinfected by means of an autoclave.

In an optional embodiment the needle guide and the needle guide holder are formed integrally.

What is claimed is:

1. An ultrasonic probe assembly for viewing internal structures of a body and collecting a tissue sample therefrom, the assembly comprising:

an elongated member having a longitudinal axis for insertion into the body through an opening therein, wherein said elongated member is adapted to be covered by a protective sheath prior to insertion into the opening in the body;

an ultrasonic scanning transducer disposed internally of said elongated member for generating an image of the internal structures of the body, said transducer being constructed and arranged to scan in the direction of the longitudinal axis of said elongated member; and a groove in said elongated member disposed at an angle to said longitudinal axis and having a first end accessible from outside the body after said elongated member is inserted into the opening and a second end for permitting a biopsy needle to access the body for collection of the tissue sample, said groove being disposed to accept a needle guide after the sheath is placed over said elongated member, whereby the needle guide enables placement by an operator of the biopsy needle for tissue sample collection assisted by imaging provided by said transducer.

2. The assembly of claim 1, further including a needle guide, wherein said elongated member retains said needle guide in said groove by friction.

3. The assembly of claim 1, further including a needle guide and a needle guide holder for retaining said needle guide in said groove.

4. The assembly of claim 1, wherein said elongated member includes a first portion generally circular in cross section transverse to said longitudinal axis with a cutout section extending along said axis and having a cross section representing a sector of the circular cross section and a second portion comprising a needle guide holder having a cross section conforming to said sector, said groove being disposed in said needle guide holder.

5. The assembly of claim 4, further including a clip removably securing said second portion to said first portion after the sheath is placed over said first portion.

\* \* \* \* \*